(12) United States Patent
Kostansek

(10) Patent No.: US 6,444,619 B1
(45) Date of Patent: Sep. 3, 2002

(54) DELIVERY SYSTEM FOR CYCLOPROPENES

(75) Inventor: Edward Charles Kostansek, Buckingham, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/950,967

(22) Filed: Sep. 12, 2001

Related U.S. Application Data

(60) Provisional application No. 60/236,087, filed on Sep. 28, 2000.

(51) Int. Cl.[7] ........................ A01N 25/10; A01N 25/28; A01N 27/00
(52) U.S. Cl. ........................................ 504/357; 504/359
(58) Field of Search .................................. 504/357, 359

(56) References Cited

U.S. PATENT DOCUMENTS

| | | | |
|---|---|---|---|
| 5,070,081 A | * | 12/1991 | Majid et al. .................. 514/58 |
| 5,518,998 A | | 5/1996 | Bäckström et al. ............ 514/3 |
| 6,017,849 A | * | 1/2000 | Daly et al. ................... 504/114 |

FOREIGN PATENT DOCUMENTS

JP 61-277610 12/1986

OTHER PUBLICATIONS

Abstract XP–002185866. Sisler, E. C., and M. Serek. "Inhibitors of ethylene responses in plants at the receptor level: Recent developments." Physiologia Plantarum, 1997. pp. 577–582.

* cited by examiner

*Primary Examiner*—S. Mark Clardy
(74) *Attorney, Agent, or Firm*—Thomas D. Rogerson

(57) ABSTRACT

The present invention relates to complexes formed from molecular encapsulation agents such as cyclodextrin, and cyclopropene and its derivatives such as methylcyclopropene, which are capable of inhibiting the ethylene response in plants, wherein the complex is pressure agglomerated.

10 Claims, No Drawings

DELIVERY SYSTEM FOR CYCLOPROPENES

This is a non-provisional application of prior pending U.S. provisional application serial No. 60/236,087 filed Sep. 28, 2000.

The present invention relates to complexes formed from molecular encapsulation agents such as cyclodextrin, and cyclopropene and its derivatives such as methylcyclopropene, which are capable of inhibiting the ethylene response in plants. Such complexes provide a convenient means for storing and transporting these compounds which are reactive gases and highly unstable because of oxidation and other potential reactions. Such complexes also provide convenient methods of delivering to plants these compounds in order to extend their shelf life.

It is well known that ethylene can cause the premature death of plants including flowers, leaves, fruits and vegetables through binding with certain receptors in the plant. It can also promote leaf yellowing and stunted growth as well as premature fruit, flower and leaf drop. Because of these ethylene-induced problems, very active and intense research presently concerns the investigation of ways to prevent or reduce the deleterious effects of ethylene on plants. U.S. Pat. No. 5,518,988 discloses the use of cyclopropene and its derivatives, including methylcyclopropene, as effective blocking agents for ethylene binding. However, a major problem with these compounds is that they are typically unstable gases which present explosive hazards when compressed. As a solution to these problems, U. S. Pat. No. 6,017,849 discloses a method of incorporating these gaseous compounds into a molecular encapsulation agent complex in order to stabilize their reactivity and thereby provide a convenient and safe means of storing, transporting and applying or delivering the active compounds to plants. For the most active cyclopropene derivative disclosed in U. S. Pat. No. 5,518,988, 1-methylcyclopropene, the preferred molecular encapsulation agent is a cyclodextrin with α-cyclodextrin being the most preferred. The application or delivery of these active compounds is then accomplished by simply adding water to the molecular encapsulation agent complex. The complex prepared according to the methods disclosed in U.S. Pat. No. 6,017,849 provides the material in the form of a powder.

Powder formulations suffer from a number of deficiencies including, for example, dustiness, difficulty in measuring small amounts (which may require that the material be prepackaged), and difficulty in controlling the release of the encapsulated material from the powder. The 1-methylcyclopropene/α-cyclodextrin complex noted above releases the 1-methylcyclopropene very quickly. It would be advantageous to moderate the release of 1-methylcyclopropene so that very little of it is released during the first few minutes after the complex is added to water. This would help prevent the escape of the 1-methylcyclopropene from the treatment area before it can be sealed and, consequently, improve the efficacy of the treatment.

We have discovered a modification to the encapsulation method of U. S. Pat. No. 6,017,849 which overcomes many deficiencies inherent in a free-flowing α-cyclodextrin based powder delivery system. Because 1-methylcyclopropene releases from the α-cyclodextrin complex so easily in the presence of water, water is not used in the present process to make the improved delivery system. We have found that pressure agglomeration of the 1-methylcyclopropene/α-cyclodextrin complex can be used to form tablets, wafers, pellets, briquettes, and similar forms, with or without added adjuvants. These delivery systems slow the release of 1-methylcyclopropene yet still allow its complete release. This same process may be equally applicable to other cyclopropene/molecular encapsulation agent complexes.

The present invention is, therefore, a composition comprising:

a) a cyclopropene of the formula:

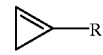

wherein R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;

b) a molecular encapsulation agent within which the cyclopropene is encapsulated; and c) optionally one or more adjuvants;

wherein the composition is pressure agglomerated.

As used herein, the term "alkyl" means both straight and branched chain ($C_1$–$C_{20}$) radicals which include, for example, methyl, ethyl, n-propyl, isopropyl, 1-ethylpropyl, n-butyl, tert-butyl, isobutyl, 2,2-dimethylpropyl, pentyl, octyl, and decyl. The terms "alkenyl" and "alkynyl" mean ($C_3$–$C_{20}$)alkenyl and ($C_3$–$C_{20}$)alkynyl groups such as, for example, 2-propenyl, 2-butenyl, 3-butenyl, 2-methyl-2-propenyl, and 2-propynyl. The term "cycloalkylalkyl" means a ($C_1$–$C_{15}$) alkyl group substituted with a ($C_3$–$C_6$) cycloalkyl group such as, for example cyclopropylmethyl, cyclopropylethyl, cyclobutylmethyl, and cyclopentylethyl. The term "haloalkyl" means an alkyl radical wherein one or more of the hydrogen atoms have been replaced by a halogen atom. The term "halogen" means fluorine, chlorine, bromine, and iodine.

Preferably, R is ($C_1$–$C_{10}$) alkyl. More preferably, R is ($C_1$–$C_8$) alkyl. Even more preferably R is ($C_1$–$C_4$) alkyl. Most preferably, R is methyl.

Preferred encapsulating agents include cyclodextrins, crown ethers, polyoxyalkylenes, polysiloxanes, and zeolites. More preferred encapsulating agents include α-cyclodextrin, β-cyclodextrin, and γ-cyclodextrin. The most preferred encapsulating agent, particularly when the cyclopropene is 1-methylcyclopropene, is α-cyclodextrin. The most preferred encapsulting agent will vary depending upon the size of the R substituent. However, as one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

The cyclopropenes applicable to this invention are known materials prepared using the processes disclosed in U.S. Pat. Nos. 5,518,988 and 6,017,849. The cyclopropene/molecular encapsulation agent complexes of the present invention are prepared by contacting the cyclopropene with a solution or slurry of the molecular encapsulation agent and then isolating the complex, again using general processes disclosed in U.S. Pat. No. 6,017,849.

It is often desirable to include in the composition of this invention one or more adjuvants, such as, for example, binders, lubricants, release agents, surfactants and/or dispersants, wetting agents, spreading agents, dispersing agents, stickers, adhesives, defoamers, thickeners, and emulsifying agents. Such adjuvants commonly used in the art can be found in the John W. McCutcheon, Inc. publication *Detergents and Emulsifiers, Annual*, Allured Publishing Company, Ridgewood, N.J., U.S.A. One or more of such adjuvants may be added to the composition prior to agglomeration or as a coating onto the agglomerated material. Optionally, adjuvants may be added to the composition at the time the cyclopropene is released as an aid to the releasing process. Preferred adjuvants include; a) binders such as, for example, sucrose, dextrose, dextrins, and other sugars and starches, polymers such as polyvinyl alcohol and lignosulfonates, and inorganics such as clays and salts, b) lubricants such as, for example, talc, magnesium stearate, stearic acid, graphite, and waxes, and c) release agents such as surfactants including, for example, sodium dodecyl sulfate.

A wide variety of pressure agglomeration equipment is available and may be used to agglomerate the composition. These include, for example, presses, granulators, and extruders. Preferred agglomeration equipment are those which are considered high pressure agglomerators such as, for example, pellet presses, tablet presses, and roller presses. Low to medium pressure equipment such as pan granulators or extruders can also be used. However, because they typically require the use of liquids, usually water, to form a slurry, dough, or paste prior to extrusion, uncontrollable and significant loss of the cyclopropene due to desorption from the complex may occur during processing.

Using such pressure agglomeration equipment, the tablets, wafers, pellets, briquettes, and similar forms of agglomerated cyclopropene/encapsulation agent complexes may range from less 0.1 mm in size to more than 5 cm. Preferably the agglomerated material is 0.5 to 2 cm in size. Preferably, the agglomerated material is a tablet or wafer. More preferably, the agglomerated material is a tablet.

Because cyclodextrins, as well as cyclopropene/ cyclodextrin complexes, possess their own binding characteristics, compositions of this invention, in which a cyclodextrin is the molecular encapsulation agent, may be prepared without additional adjuvants. Other encapsulation agents may also possess such inherent binding characteristics.

The compositions of this invention may comprise from 3 percent to 100 percent, by weight, cyclopropene/ encapsulation agent complex, 0 percent to 97 percent, by weight, binder, and from 0 percent to 3 percent, by weight, lubricant. Preferably, the compositions of this invention comprise:

| | |
|---|---|
| 1-methylcyclopropene/a-cyclodextrin complex | 25–60% |
| Binder | 40–74% |
| Lubricant | 1–2% |

More preferably, the compositions of this invention comprise:

| | |
|---|---|
| 1-methylcyclopropene/a-cyclodextrin complex | 45–55% |
| Binder | 45–55% |
| Lubricant | 0–2% |

Most preferably, the compositions of this invention comprise:

| | |
|---|---|
| 1-methylcyclopropene/a-cyclodextrin complex | 50% |
| Binder | 50% |
| Lubricant | 0–1.5% |

In practice, release of the cyclopropene from the cyclopropene/ α-cyclodextrin complex is accomplished by simply adding water, or other solvent, to the complex. Preferably, the mixture is then agitated to aid in evolution of the cyclopropene from the mixture.

Some embodiments of this invention are illustrated by the following example:

EXAMPLE

Comparison of 1-Methylcvclopropene Release from Agglomerated and Non-Agglomerated compositions A dry-blend mixture of 50%, by weight, 1-methylcyclopropene/ α-cyclodextrin ("1-MCP/ α-CD") complex powder prepared according to the process of U.S. Pat. No. 6,017,849 and 50%, by weight, dextrose powder was prepared and split into two aliquots. The first was kept as a control and the second was compression agglomerated in a DELTA™ tablet press (Aldrich, Milwaukee, Wis.) utilizing differential screw thread compression. The resulting tablets measured 9 mm in diameter by 1 mm in thickness and weighed 0.10 gm each. The density achieved in the tablet was about 1.55 g/cm$^3$ as compared to the bulk density of about 0.50 g/cm$^3$ for the 1-MCP/ α-CD complex powder. Preferably, the bulk density of the agglomerated complex will be greater than 0.6 g/cm$^3$; more preferably, the bulk density will be from 0.75 to 2.0 g/cm$^3$; even more preferably, the bulk density will be from 1.0 to 1.75 g/cm$^3$; and most preferably, the bulk density will be from 1.4 to 1.6 g/cm$^3$.

The 1-methylcyclopropene release characteristics of the agglomerated verses non-agglomerated complexes were determined by sealing a tablet of the agglomerated material in a bottle fitted with a septum, injecting water into the bottle, and analyzing the headspace for 1-MCP at 7 minute time intervals. The analysis method was gas chromatography using the following parameters:

| | |
|---|---|
| Instrument | Hewlett Packard (Agilent Technologies) 6890 |
| Detector | Flame Ionization |
| Detector Temperature | 150 deg. C. |
| Air Flow Rate | 450 ml/min. |
| Hydrogen Flow Rate | 40 ml/min. |
| Make up Gas Flow Rate | 25 ml/min. |
| Column | Chrompack CP-PoraPlot Q-HT Dimensions: 10 m x 0.32 mm i.d. Film Thickness: 10 microns |
| Carrier Gas | Helium |
| Flow Rate | 2.5 ml/min |
| Column Head Pressure | 6 psi |
| Injection Port Temperature | 150 deg. C. |
| Initial Temperature | 35 deg. C. |
| Initial Time | 0.5 min. |
| Program Rate 1 | 20 deg. C./min. |
| Final Temperature | 250 deg. C. |
| Final Time | 6.5 min. |
| Injection Volume | 1 ml |
| Injector | Manual/Splitless (1 ml inlet glass liner) |

Release of 1-methylcyclopropene from an equivalent amount of the dry blended powder control (non-agglomerated complex) was evaluated in the same manner. Table 1 shows the resulting average release profiles produced from two separated samples each of the tablet and powder delivery systems.

Clearly, the tablet had a significantly reduced initial release rate compared to the powder, yet the total amount released was about the same after 35–42 minutes. Even at the first point measured (equivalent to time zero), the powder had already released 6.5% of the active ingredient whereas the tablet had released less than 1%. At 7 minutes, the powder had released 43% of the active ingredient versus only 12.5% for the tablet. In addition to the release characteristics, the tablets were non-dusty compared to the powder control.

TABLE 1

| Time after water addition (min.) | % 1-MCP Released From Powder | % 1-MCP Released From Tablet |
|---|---|---|
| 0 | 6.5 | 0.5 |
| 7 | 43 | 12.5 |
| 14 | 53.5 | 32.5 |
| 21 | 67.5 | 53.5 |
| 28 | 75 | 64 |
| 35 | 82.5 | 79 |
| 42 | 91.5 | 89.5 |

I claim:

1. A composition comprising:
a) a cyclopropene of the formula:

▷—R wherein R is hydrogen or a substituted or unsubstituted alkyl, alkenyl, alkynyl, cycloalkyl, cycloalkylalkyl, phenyl, or naphthyl group;
wherein the substituents are independently halogen, alkoxy, or substituted or unsubstituted phenoxy;
b) a molecular encapsulation agent within which the cyclopropene is encapsulated; and
c) optionally one or more adjuvants;
wherein the composition is pressure agglomerated.

2. The composition of claim 1, wherein R is $(C_1-C_8)$alkyl.

3. The composition of claim 1, wherein R is methyl.

4. The composition of claim 1, wherein the molecular encapsulation agent is a cyclodextrin or a mixture of cyclodextrins.

5. The composition of claim 1, wherein the molecular encapsulation agent is α-cyclodextrin.

6. The composition of claim 1, wherein the optional adjuvant is:
a) a lubricant; or
b) a release agent, or
c) a mixture of a lubricant and a release agent.

7. The composition of claim 1, wherein the composition is pressure agglomerated using a tablet press.

8. A method for preparing a composition of an encapsulated cyclopropene comprising pressure agglomerating a composition comprising:
a) a cyclopropene of the formula:

▷—R wherein R is hydrogen or a substituted or unsubstituted alkyl, alkenyl, alkynyl, cycloalkyl, cycloalkylalkyl, phenyl, or naphthyl group;
wherein the substituents are independently halogen, alkoxy, or substituted or unsubstituted phenoxy;
b) a molecular encapsulation agent within which the cyclopropene is encapsulated; and
c) optionally one or more adjuvants.

9. The method of claim 8, wherein the molecular encapsulation agent is α-cyclodextrin.

10. The method of claim 8, wherein the optional adjuvant is:
a) a lubricant; or
b) a release agent, or
c) a mixture of a lubricant and a release agent.

* * * * *